(12) United States Patent
Scher et al.

(10) Patent No.: US 7,271,200 B2
(45) Date of Patent: *Sep. 18, 2007

(54) EMULSIONS

(75) Inventors: Herbert Benson Scher, Morago, CA (US); Patrick Joseph Mulqueen, Oxfordshire (GB); Nicholas David Green, Berkshire (GB); Catherine Julia Piper, Berkshire (GB)

(73) Assignee: Syngenta Limited (GB)

( * ) Notice: Subject to any disclaimer, the term of this patent is extended or adjusted under 35 U.S.C. 154(b) by 246 days.

This patent is subject to a terminal disclaimer.

(21) Appl. No.: 10/800,901

(22) Filed: Mar. 15, 2004

(65) Prior Publication Data

US 2004/0176479 A1 Sep. 9, 2004

(51) Int. Cl.
*B01F 3/08* (2006.01)
*B01J 13/02* (2006.01)

(52) U.S. Cl. .......... 516/59; 504/363; 504/364; 504/365; 514/941; 514/942; 516/53; 516/67; 516/69; 516/71; 428/402.2; 427/213.3; 264/4.1; 264/4.7

(58) Field of Classification Search .......... 516/59; 528/49
See application file for complete search history.

(56) References Cited

U.S. PATENT DOCUMENTS

| | | | |
|---|---|---|---|
| 3,607,776 A | 9/1971 | Santo et al. | |
| 3,778,383 A | 12/1973 | Schibler et al. | |
| 3,965,032 A | 6/1976 | Gibbs et al. | |
| 3,996,154 A | 12/1976 | Johnson et al. | |
| 4,324,683 A | 4/1982 | Lim et al. | |
| 4,778,781 A | 10/1988 | Washizu et al. | |
| 4,977,059 A | 12/1990 | Liang et al. | |
| 5,075,279 A | 12/1991 | Sano | |
| 5,120,475 A | 6/1992 | Chen et al. | |
| 5,160,529 A | 11/1992 | Scher et al. | |
| 5,223,477 A | 6/1993 | Scher et al. | |
| 5,283,015 A | 2/1994 | Hutchings et al. | |
| 5,332,584 A | 7/1994 | Scher et al. | |
| 5,342,556 A | 8/1994 | Traubel et al. | |
| 6,017,559 A | 1/2000 | Lubetkin et al. | |
| 6,407,196 B1 * | 6/2002 | Shen et al. | 528/49 |

FOREIGN PATENT DOCUMENTS

| | | |
|---|---|---|
| EP | 0 336 666 A | 10/1989 |
| EP | 0 551 796 A | 7/1993 |

* cited by examiner

*Primary Examiner*—James J. Seidleck
*Assistant Examiner*—Saira B. Haider
(74) *Attorney, Agent, or Firm*—Rebecca Gegick

(57) ABSTRACT

A novel emulsion comprising a material which is stabilised by a polymer resin precursor having interface active molecules incorporated therein by reaction from poorly or non-surface active materials is disclosed. The process for producing such emulsions is likewise disclosed.

15 Claims, No Drawings

EMULSIONS

FIELD OF THE INVENTION

This invention relates to emulsions of the nano and micron size and to a process for their production. More particularly, this invention relates to emulsified droplets of a liquid material which is substantially insoluble in water, and where the stabilising interface has surface active agents incorporated therein, thereby forming an interface having a number of advantages. Further, this invention relates to the processes for the production of such emulsions and methods for their use.

BACKGROUND OF THE INVENTION

The use of emulsions is well known in the chemical art, including the pharmaceutical, specialty chemical and agricultural industries. In agriculture, emulsions provide appropriate formulations vehicles for delivery of herbicides, insecticides, fungicides, bactericides and fertilizers. Non-agricultural uses have included formulation of dyes, inks, pharmaceuticals, flavoring agents and fragrances.

Surfactants are required to aid in the emulsification process of oil into water (and vice versa) and to stabilise the thus formed emulsion against physical degradation processes.

A surfactant can adsorb to (and be desorbed from) an interface relatively easily. This process can lead to destabilisation of an emulsion; moreover, micellisation effects will also lead to redistribution of components throughout the system, often leading to Ostwald ripening and other undesirable interactions. All the many approaches to stabilisation of emulsions rely on one or more of the above described effects with typical surfactant adsorption as the stabilising mechanism.

Oil-in-Water emulsions (EW's) consist of a dispersion of oil droplets in a continuous aqueous medium. Such products are widely employed and encountered in various industries e.g., food (e.g. mayonnaise), detergency (e.g. removal of oil deposits), pharmaceuticals (e.g. drug administration), cosmetics (e.g. skin creams) and agricultural products (both as concentrates and diluted into water for application).

EW's are important in agriculture as a means of formulating oil-based systems in a more environmentally attractive form than the conventional Emulsifiable Concentrate (EC) where less solvent is sometimes possible per unit active ingredient and also as a precursor to Suspension-Emulsions (SE's) or Suspo-Emulsions which consist of a mixture of an oil-in-water and a suspension concentrate (SC). Such EW or SE products tend to have lower skin and eye toxicity ratings than the corresponding EC products as well as higher flash points and better compatibility with HDPE containers.

EW's, unlike EC's in the undiluted state, are only stable in the kinetic sense. This is because the system is inherently thermodynamically unstable and can only be formed non-spontaneously. This can be understood if one considers a large drop of oil, say with a volume of 1 ml, which is emulsified into many droplets each containing on average 0.001 ml. The interfacial area is greatly increased as a result of the sub-division of the bulk oil into much smaller units. This large interfacial energy is accompanied by a large surface energy that is given by the product of interfacial tension and increase in surface area $\Delta A$ (where $\Delta A = A_2 - A_1$ with $A_2$ being the total area of the subdivided droplets and $A_1$ that of the bulk oil). In the absence of any absorbed molecules at the interface the interfacial tension $\mu_{SL}$ is relatively large and hence the interfacial free energy for creating the interface $\Delta A \mu_{SL}$ can be quite large. Thus the interfacial free energy opposes the process of emulsification.

It should be mentioned, however, that in an emulsification process, a large number of small droplets are formed and this is accompanied by an increase in the total entropy of the system. This increase in entropy facilitated the emulsification process although its value is relatively small compared to the interfacial free energy. From the second law of thermodynamics, the free energy of emulsification is given by the expression $\Delta G^{form} = \Delta A \mu_{SL} - T \Delta S^{Conf}$ where $\Delta S^{Conf}$ is the configurational entropy term In most dispersion processes $\Delta A \mu_{SL} \gg -T \Delta S^{Conf}$ and therefore $\Delta G^{form}$ is large and positive. Thus the process of emulsification is non-spontaneous and hence with time the droplets tend to aggregate and/or coalesce to reduce the total energy of the system.

To prevent flocculation and/or coalescence one needs to create an energy barrier between the droplets to prevent their close approach. This energy barrier is the result of the creation of a repulsive force that overcomes the ever present van der Waals' attraction. The balance between repulsive and attractive forces determines the stability of the system against flocculation and coalescence. Assuming one can arrange to achieve a sufficient barrier to prevent close approach between the particles (i.e. stability in the colloid sense) what other factors play a role in keeping the droplets uniformly suspended in the continuous phase? One of the most important factors is gravity, which can cause separation of the droplets into a compact layer of cream depending on the density difference between the droplets and the medium, and their size.

There are basically five ways in which the structure of a dispersion of liquid droplets in a continuous medium can change. These are summarised as follows:

1. No change in droplet size (or droplet size distribution), but build-up of an equilibrium droplet concentration gradient within the emulsion. In limiting cases, the result is a close packed array (usually random) of droplets at one end of the system with the remainder of the volume occupied by the continuous phase liquid. This phenomenon results from external force fields, usually gravitational, centrifugal or electrostatic, acting on the system. "Creaming" is the special case in which the droplets collect in a concentrated layer at the top of an emulsion. A parallel effect may be seen when the oil phase has a density greater than 1.00 such that the cream sediments on the bottom of the container rather than rising to the top of the container when the density of the oil phase is less than 1.00.

2. Again, no change in basic droplet size or distribution but the build-up of aggregates of droplets within the emulsion. The individual droplets retain their identity. This process of flocculation results from the existence of attractive forces between the droplets.

3. In which flocculated droplets in an aggregate in the bulk of the emulsion, or alternatively, droplets within a close-packed array resulting from sedimentation or creaming, coalesce to form larger droplets. This results in a change in the initial droplet size distribution. The limiting state here is the complete separation of the emulsion into the two immiscible bulk liquids. Coalescence thus involves the elimination of the thin liquid film (of continuous phase) which separates two droplets in contact in an aggregate or a close-packed array. The forces to be considered here are therefore the forces acting within thin-liquid films in general. These can be complex and varied. In mixed emulsion systems, for example, in which there are droplets of liquid 1 and also liquid 2 dispersed in a continuous phase of liquid 3, coalescence between liquid 1 and liquid 2 droplets only occurs if liquids 1 and 2 are miscible with each other. If they are immiscible, then either droplet adhesion or droplet engulfment occurs. In either case, the thin liquid film between the contacting droplets is eliminated. When two droplets approach each other, surface fluctuations result since the interface is deformable. The amplitude of these fluctuations may grow to a considerable extent such that droplet coalescence occurs. However, this growth is opposed by the interfacial tension gradients that result in film expansion during growth of fluctuation. As a result of film expansion, regions of relatively higher interfacial tension than the rest of the film are created. This creates a gradient in the interfacial tension which tends to dampen the fluctuation. The driving force for this process is the Gibbs elasticity. The higher the Gibbs elasticity, the lower the tendency to coalesce.

Another factor which may retard coalescence is the surface viscosity which plays a role with many macromolecular films e.g. proteins. Indeed, such films are viscoelastic and they prevent coalescence by combination of the high viscosity in the film and elasticity which prevents fluctuation growth. Interfacial elasticity and viscosity may not be sufficient criteria for the prevention of coalescence, particularly when film drainage is fast. It is, therefore, essential to obtain information on the rate of drainage and equilibrium film thickness to assess emulsion stability.

4. An alternative way in which the average droplet size in an emulsion can increase, without the droplets coalescing, occurs if the two liquids forming the disperse phase and the continuous phase, respectively, are not totally immiscible. This is the case in reality because all liquid pairs are mutually miscible to some finite extent. If one starts with a truly monodisperse emulsion system, then no effects arising from this mutual solubility will arise. However, if the emulsion is polydisperse, larger droplets will form at the expense of the smaller droplets owing to the process known as Ostwald Ripening. In principle, the system will tend to an equilibrium state in which all the droplets attain the same size (this may be, of course, that state when we have just one single large drop). The process of Ostwald ripening results from the difference in solubility between small and large droplets. Since the solubility S of a particle of radius $\alpha$ is proportional to $2\mu/\alpha$ where $\mu$ is the interfacial tension, then S is larger the smaller the droplet radius. Thus, for two particles with radii $\alpha 1$ and $\alpha 2$, where $\alpha 1 < \alpha 2$, the solubility S1 is larger than S2 and, $$\frac{RT}{M}\ln\frac{S_1}{S_2} = \frac{2\mu}{p}\left(\frac{1}{a_1} - \frac{1}{a_2}\right)$$

where M is the molecular weight of the substance that has a density p. Thus the driving force of Ostwald ripening is the difference between $S_1$ and $S_2$. This means that, with time, the smaller droplets tend to dissolve and the solute diffuses in bulk solution and becomes deposited on the larger particles. This causes a shift in the particle size distribution towards the coarser size. This is clearly undesirable, since it accelerates sedimentation on the one hand and may produce a reduction in bio availability on the other.

5. A further way in which the structure of an emulsion may change is for the emulsion to "invert", e.g. for an o/w emulsion to change to a w/o emulsion. This may be brought about by a change in temperature or concentration of one of the components or by the addition of a new component to the system. This may occur when the oil volume fraction exceeds a critical value $\emptyset_{cr}$ that is usually the maximum possible packing fraction. For example, for a dispersion of uniform spheres, $\emptyset_{cr}$ is 0.74 and any increase in $\emptyset$ above $\emptyset_{cr}$ usually results in inversion. Clearly with a polydisperse system, $\emptyset_{cr}$ can exceed 0.74.

So the four main processes referred to above can be summarised as sedimentation (creaming), flocculation, coalescence and Ostwald Ripening. Certainly, in practical systems, all four processes may appear to occur simultaneously or sequentially in any order and this will depend upon the relative rate constants for the four basic processes under the conditions of storage of the emulsion.

Approaches to stabilisation of emulsions generally take the form of attempting to induce a repulsion between droplets by electrostatic or steric means—and this usually means the use of surfactants.

The best surfactants (emulsifiers) tend to be those of the block or graft type consisting of two main groups: the anchoring group B which must be chosen to have minimum solubility in the continuous medium and high affinity for the oil surface and A which must be chosen with maximum solvation by the continuous medium and minimum affinity for the oil surface. The ratio of groups A and B must be adequately chosen such that maximum adsorption occurs. It is clear that one should minimise micellisation of the block or graft polymer in order to allow adsorption to become more favourable. The length of the A chains must be optimised to give adsorbed layers with sufficient length such that the energy minimum seen in a typical energy interaction/distance curve for a sterically stablised particle becomes small. Various combinations of A and B groups may be produced of which A-B, A-B-A block copolymers and $BA_n$ graft copolymers are the most common.

It is also essential to choose materials that enhance the Gibbs elasticity. For this reason, surfactant mixtures, polymer/surfactant combinations, or liquid crystalline phases are most effective in producing stable emulsions.

To prevent sedimentation/creaming of emulsions it is essential to build up a "structure" (gel network) in the system that has (a) a high low-shear viscosity to overcome gravity and (b) sufficient elasticity (modulus or yield stress) to overcome compression of the whole network. Both can be achieved by the addition of a second phase that forms an "elastic" three-dimensional network in the medium. Several systems are available, of which xanthan gum (a microbial polysaccharide), sodium montmorillonite, microcrystalline cellulose and finely divided (fumed) silica are perhaps the most commonly used. Xanthan gum forms a highly elastic system as a result of polymer chain overlap. Sodium montmorillonite and microcrystalline cellulose form a gel structure as a result of interaction of extended double layers around the the thin clay platelet and/or edge-to-face flocculation. Fumed silicas form an elastic network as a result of the formation of chain aggregates. It is common to use mixtures of xanthan gum with sodium montmorillonite, microcrystalline cellulose or silica.

Various other methods may be used to build up a gel structure in emulsions. An example is controlled flocculation of electrostatically or sterically-stabilised dispersions. With electrostatically-stabilised dispersions, controlled flocculation is produced by addition of electrolyte which results in the formation of a sufficiently deep secondary minimum (of the order of 1-5 kT). This method must be applied with extreme care since coagulation may occur if the electrolyte concentration reaches a certain limit. With sterically-stabilised dispersions, controlled flocculation may be achieved by reducing the adsorbed layer thickness. Another method of controlled flocculation is that induced by the addition of a free non-adsorbing polymer to a sterically-stabilised suspension. Above a critical volume fraction of the free polymer (such as polyethylene oxide) weak flocculation occurs. This is usually referred to as depletion flocculation.

Much work has been carried out to produce "stable" emulsions as well as to more fully understand the processes whereby such emulsions deteriorate.

Approaches to the production of "stable" emulsions include:
1. Matching the densities of the oil phase to the aqueous phase (to minimise creaming or sedimentation) but this is difficult to achieve in practice due to variation of density with temperature as well as such a limitation resulting in low levels of active ingredient in a formulation.
2. Preparation of emulsions with a narrow particle size distribution. This is because a monodisperse emulsion cannot Ostwald ripen and clearly the narrower a distribution that can be achieved during processing, the less will be the drive to Ostwald ripen in the system.
3. Selection of the "best" surfactants to achieve charge-stabilisation, steric-stabilisation.
4. Use of colloid stabilisers such as polyvinylalcohol.
5. Stabilisation by adsorbed solid particles at the liquid/liquid interface, the so-called Pickering Emulsion.

It has been found that several of these approaches may have to be employed in a single formulation to achieve a storage-stable product. Even then, the products will only be kinetically stable (i.e. have a limited shelf-life-which may be two to three years) and given time will degrade.

A key mechanism of destabilisation is Ostwald Ripening, although it has received little attention in the public literature. Ostwald ripening is classically considered to occur because of the chemical potential difference between droplets (or particles) of different sizes and the transfer of oil from small to large particles such that the shape of the emulsion distribution and the size changes, moving upfield to a larger value with time. It has been considered that this transfer should be through the aqueous phase by dissolving oil in the continuous phase. In fact, water-insoluble oils do not "Ostwald" ripen when prepared as oil-in-water emulsions and this fact has been recognised in the literature.

However, until recently, it has not appeared to have been recognised that oils which are of a low water solubility and which might not be expected to Ostwald ripen quickly, can, in fact, do so rapidly, dependent upon the choice of surfactants employed to prepare and stabilise the emulsion. This is probably due to micelle transport of oil from small to large droplets. So we have, in most practical surfactant stabilised emulsions, two processes (at least) of effectively obtaining Ostwald ripening:

(a) Finite solubility in the aqueous phase of the dispersed oil, (b) Ability of the oil to be dissolved in the surfactant micelle.

If either (or preferably both) of these processes can be prevented, then Ostwald ripening should not occur. This does not mean, of course, that a stable emulsion will then automatically be achieved, because other factors, especially the choice of surfactant type and amount, cosurfactant, temperature range for storage of the product then become critical in the overall formulation definition. However, if Ostwald ripening can be prevented, this would be a major benefit to all manufacturers and users of emulsions.

From the above, it is clear that a surfactant can adsorb to (and be desorbed from) an interface relatively easily. This process can lead to destabilisation of an emulsion; moreover, micellisation effects will also lead to redistribution of components throughout the system, often leading to Ostwald ripening and other undesirable interactions. All the many approaches to stabilisation of emulsions rely on one or more of the above described effects with typical surfactant adsorption as the stabilising mechanism.

If surfactants could be bound in such a manner that they could not be desorbed, then more stable emulsions could be produced, opening up new possibilities for processing of emulsions and uses for emulsions under adverse conditions.

Regardless of the type of process utilized, the final emulsion product may be packaged as a liquid containing oil droplets therein, or as a dried or solid formulation such as granules, tapes or tablets containing oil droplets which may be later added to a liquid solution such as a spray tank for agricultural use. This liquid often has various ingredients in addition to water, including wetters, dispersants, emulsifiers, protective colloids or colloid stabilizers and surface active agents or surfactants. The protective colloids serve to prevent agglomeration of the oil droplets. The surfactants perform various functions depending upon the type of surfactant used. These include varying the permeability of the wall, aiding in dispersing the emulsion, acting as a wetter, reducing or eliminating foaming, affecting the adhesiveness of the emulsion to the surface to which it is applied, and so forth. Primarily, conventional surfactants act as free, non-bound emulsifiers in the preparation of the emulsion.

SUMMARY OF THE INVENTION

We have found that by reacting a potentially wall-forming material conventionally used in microcapsule formation with an interface modifying compound at an interface, there can be produced "in-situ" surfactants which offer a number of advantages. Neither the wall forming material nor the interface modifying compound need have surfactant properties of themselves but react together to form a surfactant.

These novel surfactants can be produced by a range of reactions either directly in the oil phase or interfacially. The surfactants can be essentially polymeric in nature if an oligomeric compound is employed as reactant. The surfactants are bound to the interface by virtue of their formation in-situ at the interface and in consequence are non-micelle forming, imparting high stability and efficiency to the systems in which they are employed.

The novel surfactants are produced by reaction of an interface modifying compound with wall-forming materials conventionally used in microcapsule manufacture. However it is the purpose of the present invention to provide an emulsion in which dispersed droplets are stabilised by a layer of surfactant material which is insubstantial in that it provides no significant barrier to the release of the content of the dispersed phase droplet (or "core material" in microencapsulation terms.

It has now been discovered that one or more compounds with wall modifying properties in microencapsulation processes can, by virtue of reaction with other wall-forming materials, be incorporated at the emulsion interface to create a stable emulsion surface with surfactant and colloid stabilizing properties. While the modifying compounds may have surface activity, the preferred molecules have weak or nonexistent surface activity and colloid stabilizing properties in and of themselves. Further, these molecules typically have one to four functional groups. By the inclusion of an interface modifying compound, which may not of itself exhibit any surface activity, to the wall-forming material at the oil-water interface, the emulsion may exhibit those properties of a conventional emulsion normally stabilized by a surface active agent. These agents or compounds serve to change the properties of the emulsion such that the emulsion may, for example, become more or less adhesive to a particular the surface, exhibit improved dispersibility properties, or act as a protective colloid, depending upon the type of agent added to the interface.

The novel surfactant systems offer at least one of and preferably all of the following advantages and characteristics:

1. Improved stability of the emulsion with respect to:
   1.1 Prevention of agglomeration, coagulation, droplet size growth
   1.2 Improved thermal storage stability
   1.3 Improved resistance to co-solvent formulation
   1.4 Improved resistance to shocking additives
   1.5 Improved electrolyte tolerance
   1.6 Improved formulation compatibility 2. Properties arising from having no free surfactant
   2.1 Low foaming
   2.2 No Ostwald ripening processes (or minimal)
   2.3 Improved SE stability (minimal micellisation effects)

3. Control of particle size and PSD
   3.1 More efficient use of surfactants with less small particles 4. Ability to tailor chemistry to specific oils and end use requirements 5. Control of surface charge and charge density for specific uses.

These novel surfactants can be produced by a range of reactions either directly in the oil phase or interfacially. The surfactants are thus bound to the interface, non-micelle forming which impart high stability and efficiency to the systems in which they are employed.

Emulsions having interface modifying agents built into their oil-water interface are capable of affecting various properties. These include improved stability of the emulsions, for example, prevention of agglomeration of the emulsion, reduction or elimination of particle size growth, improved thermal storage stability, and improved formulation compatibility. By having reduced levels of or no free surfactant, in contrast to present emulsions, foaming is reduced or eliminated and the size of the emulsion can be better controlled. Particle size in traditional emulsions is controlled by shear and amount of added conventional emulsifier (surfactant) used to make the emulsion. High levels of surfactants, which normally work by absorption at the interface, can often adversely affect the stability of the resultant emulsion (eg by micelle-induced Ostwald Ripening). The present invention resides in both the process for preparing such emulsions and the emulsions thus formed.

One aspect of this invention describes emulsion compositions having one or more interface modifying agents bonded therein. These agents may be anionic, cationic, zwiterionic, amphiphilic, steric, hydrolysable, compatibilizing, and/or polymeric in nature. Charged agents may or may not be switchable between ionized and non-ionized forms. Examples of polymeric agents include polyesters, polyurethanes, acrylics and methacrylics, styrenics and copolymers, grafts, stars, oligomers, macromonomers and blends thereof.

The presence of ionic groups at the surface of emulsions provides a means of charge repulsion between adjacent particles and this aids colloid stability of the formulation. Charge repulsion may be between either positive or negative groups. Colloid stabilization may alternatively be affected by non-charged hydrophilic moieties which maintain stability by preventing the steric stabilizers between particles interacting. The preferred method of stabilization will depend upon the desired application of the emulsion product. For example, positively charged structures may adhere strongly to negatively charged biological material.

Another aspect of this invention describes a process for the introduction of one or more stabilizers, including alcohols, thiols, amines and isocyanate reactive species, into the interface of an emulsion.

DETAILED DESCRIPTION OF THE INVENTION

It has been found that, by changing the method of emulsion interface formation in the conventional emulsion processes, it is possible to produce a modified chemical structure which alters the properties of the emulsion. The process employs interface modifying compounds which may or may not exhibit any surface activity of themselves, but when incorporated into the interface of the emulsion, form surfactants providing emulsions with enhanced properties. The novel surfactants are produced by reaction of an interface modifying compound with wall-forming materials conventionally used in microcapsule manufacture. Such wall-forming materials are monomers, oligomers or pre-polymers which in conventional microencapsulation undergo polymerization to form a microcapsule wall at the interface of the dispersed phase emulsion droplet and the continuous phase. In the process of the present invention however, substantially all of the polymer-forming moieties in the monomer, oligomer or pre-polymer are reacted with a reactive moiety on the interface modifying compound such that a surfactant is formed and little or no wall-forming functionality remains after reaction. In consequence the dispersed droplets are stabilised by a layer of surfactant material which is insubstantial in that it provides no significant barrier to the release of the content of the dispersed phase droplet (or "core material" in microencapsulation terms).

Thus according to the present invention there is provided an emulsion comprising a dispersed phase droplet having a surfactant layer at the interface with the continuous phase wherein said surfactant layer is formed by the reaction of the wall-forming moieties of a microcapsule wall-forming material with an interface modifying compound selected from compounds having a formula (I), (II), (III) (IV) or (V)

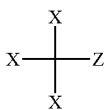

(V)

wherein Z is a moiety that contributes to modifying the surface properties of said emulsion and each X is, independently, a functional moiety capable of reacting with the wall-forming moieties of a wall-forming material and the moieties designated by lines linking the X and Z functional groups have a molecular weight of between 50 and 4000, and may be optionally substituted aryl, hydrocarbyl, or heterocyclic units, or combinations thereof, optionally containing internally linked amino, ether, thioether, acetal, ester, thioester, amide, sulphonamide, urethane, urea, carbonate, siloxane, or phosphonamide groups or combinations thereof and wherein substantially all of the wall-forming moieties of the wall-forming material are reacted with one or more groups —X of the interface modifying compound such that little or no wall-forming functionality remains after reaction.

According to a further aspect of the present invention there is provided an emulsion with enhanced stability having discrete droplets of a material enclosed within an organic phase dispersed throughout a continuous aqueous phase comprising an interface between the organic phase and aqueous phase wherein the interface has a polymer resin having incorporated therein at least one interface modifying compound selected from compounds having the formula X-z     (I)

X-z-X     (II)

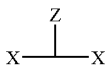

(III)

X—X-z     (IV)

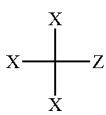

(V)

wherein Z is a moiety that contributes to modifying the surface properties of said microcapsule and each X is, independently, a functional moiety capable of reacting with isocyanate and the moieties designated by lines linking the X and Z functional groups have a molecular weight of between 50 and 4000, and may be optionally substituted aryl, hydrocarbyl, or heterocyclic units, or combinations thereof, optionally containing internally linked amino, ether, thioether, acetal, ester, thioester, amide, sulphonamide, urethane, urea, carbonate, siloxane, or phosphonamide groups or combinations thereof, thereby imparting surface activity when incorporated.

Typically, the interface modifying molecules of the present invention have molecule weights of about 2000 or less. For those interface modifying compounds which have strong ionic groups, such as sulfonates, the molecules may have molecule weights of about 1000 or less. It may be preferred to have molecular weights of less than 10,000 in prepolymers which have been reacted with the interface modifying agent.

Preferably —X is hydroxyl, thiol, amino or carboxylate. It is especially preferred that —X is amino. When X is amino it is preferably a group —NHA wherein A is hydrogen or $C_1$ to $C_4$ alkyl. When X is carboxylate it is suitably a group —CO—OR where R is hydrogen or a hydrocarbyl moiety having 1-30 carbon atoms optionally linked or substituted by one or more halo, amino, ether or thioether groups or combinations of these. It is preferred that R is hydrogen for isocyanate wall-forming systems. For aminoplast wall-forming systems, R is preferably hydrogen or $C_1$ to $C_{12}$ straight or branched chain alkyl. In structure (IV) above, the group —X— should be capable of undergoing reaction with the wall-forming material and is preferably an amino linking group —NH—. Where more than one moiety —X is present, the respective groups X may be the same or different.

The surface modifying compounds of the present invention contain one or more functional groups (designated Z) capable of imparting surface activity at the surface of the microcapsule. The nature of the group Z is such that it interacts strongly with the continuous aqueous phase in the process for preparation of the microcapsules, for oil-in-water systems, which are the preferred systems of this invention. However, the invention is also useful in connection with water-in-oil systems; there the group Z must interact strongly with the organic continuous phase. Z may be charged or non-charged, but in the context of the present invention, is hydrophilic in nature for oil-in-water systems. Preferably -Z comprises sulphonate, carboxylate, phosphonate, phosphate, quaternary ammonium, betaine, oxyethylene or an oxyethylene-containing polymer. When -Z is sulphonate, carboxylate, phosphonate or phosphate it may be in the form of the free acid but is preferably present in the form of a salt (i.e. $-Z^-$ anion), for example an alkali metal salt. When -Z is quaternary ammonium (as that expression is used herein) it suitably has the structure $$[—NR_1R_2R_3]^+A'^-$$

wherein $R_1$, $R_2$ and $R_3$ are independently hydrogen or $C_1$ to $C_4$ alkyl and $A'^-$ is a suitable inorganic or organic anion such as halide or acetate . Preferably not more than one of R is hydrogen. It will be appreciated that when -Z is a positively or negatively charged species it may be converted from a charged species to a non-ionised form and visa versa, depending on the pH. Thus for example it may be convenient to incorporate a molecule containing the group -Z in non-ionised form and then convert it into an ionised form subsequently.

When -Z is oxyethylene or an oxyethylene-containing polymer, it is preferably an oxyethylene polymer or a random or block oxyethylene/oxypropylene copolymer, preferably containing an oxyethylene to oxypropylene ratio of grater than 1. Typically therefore Z may take the form

     (VI)

wherein $R_4$ is an end-capping group such as $C_1$ to $C_4$ alkyl, especially methyl, r, and s are independently from 0 to 3000 or more preferably 0 to 2000, provided that s is not 0 and the total of r+s is from about 7 to about 3000 or more preferably from about 10 to about 2000 and EO and PO represent oxyethylene and oxypropylene respectively which may be arranged in random or block formation. Preferably, r and s are independently from 0 to 100, provided that the total of r+s is from about 10 to about 100. It is especially preferred that r and s are independently from 0 to 25 and the total for r+s is from 10 to 25. Preferably s is greater than r, for example s is preferably at least 4 times greater than r. When -Z represents an ethylene oxide-propylene oxide block copolymer, it may have the structure

wherein $R_4'$ is an end-capping group such as $C_2$ to $C_4$ alkyl, especially methyl, r', s' are independently from 0 to 2000, provided that s' is not 0 and the total of r'+s'+t is from about 7 to about 3000 or more preferably from about 10 to about 2000 and EO and PO represent oxyethylene and oxypropylene respectively. Preferably s' is greater than the sum of r'+t, for example it is preferred that s' is at least 4 times greater than the sum of r'+t. Preferably r', s' and t are independently from 0 to 100, provided that the total of r'+s'+t is from about 10 to about 100.

When Z has the structure -Z- in formula (II) above it is suitably an oxyethylene-containing polymer having the formula as shown in (IIA) below.

It is preferred that X and Z are not both carboxylate at the same time.

It will be appreciated that if X and Z are groups which are capable of reacting together, for example carboxylate and/or sulphonate, X and Z may together form a ring structure capable of ring opening under the conditions of the wall-modifying reaction.

The moieties linking the X and Z functional groups have a molecular weight of between 50 and 4000, and may be optionally substituted aryl, hydrocarbyl, or heterocyclic units, or any combination thereof, optionally containing internally linked amino, ether, thioether, acetal, ester, thioester, amide, sulphonamide, urethane, urea, carbonate, siloxane, or phosphonamide groups or combinations of these. Certain ether groups such as —$CCH_3CH_2O$— units are known to promote the solubility of the modifying molecule in the oil phase. When more than one functional group X is present, the groups may be separated by from 2 to 400 atoms, and more preferably from 2 to 150 atoms.

The moieties linking the X and Z functional groups have a preferred molecular weight of between 70 and 2000 and more particularly typically comprise, singly or in combination:

one or more straight or branched aliphatic chains having a total of 1-400 carbon atoms, preferably 2-200 carbon atoms and more preferably 2-100 carbon atoms optionally containing one or more saturated or unsaturated aliphatic or aromatic carbocyclic groups having 3-14 carbon atoms in the ring(s) wherein the aliphatic or carbocyclic carbons are optionally internally linked or substituted by one or more halo, amino, ether, thioether, acetal, ester, thioester, amide, sulphonamide, urethane, urea, carbonate, siloxane, or phosphonamide groups or combinations of these. Illustrative examples of ring structures which are optionally present include phenyl, naphthyl, cydopentyl, cyclohexyl, and the like.

one or more alkenyl or alkynyl groups optionally linked or substituted by one or more alkyl, halo, amino, ether, thioether, acetal, ester, thioester, amide, sulphonamide, urethane, urea, carbonate, siloxane, or phosphonamide groups or combinations of these.

one or more heterocyclic groups having a ring size of from 4-10 atoms and containing 1-3 heteroatoms selected independently from nitrogen, oxygen, sulphur, sulphone or sulphoxide (such as tetrahydrofuryl, pyridyl, and the like) and optionally linked or substituted by one or more alkyl, halo, amino, ether, thioether, acetal, ester, thioester, amide, sulphonamide, urethane, urea, carbonate, siloxane, or phosphonamide groups or combinations of these.

one or more saturated or unsaturated aliphatic or aromatic carbocyclic groups having 3-14 carbon atoms in the ring(s) wherein the aliphatic or carbocyclic carbons are optionally internally linked or substituted by one or more halo, amino, ether, thioether, acetal, ester, thioester, amide, sulphonamide, urethane, urea, carbonate, siloxane, or phosphonamide groups or combinations of these. Illustrative examples of ring structures include phenyl, naphthyl, cyclopentyl, cyclohexyl, and the like.

The alkyl groups that are optional substituents typically have 1-8, 1-6, 1-4, or 1-3 carbon atoms, such as methyl, ethyl, propyl, and the like.

The nature of Z and/or of the moieties linking the X and Z functional groups affects (i) the solubility of the surface modifying compound in the discontinuous oil phase and its differential solubility between the continuous aqueous phase and the discontinuous oil phase to be encapsulated, (ii) the process of choice, and/or (iii) the properties of the modified capsule as will be discussed in greater detail below.

The moieties linking the X and Z functional groups in the generalized structures (I) to (IV) above are illustrated by but are not limited to surface modifying compounds as follows.

A preferred structure (I) has the formula $$X—Y_1\text{-}Z \quad\quad (IA)$$

wherein $Y_1$ represents the moiety linking X and Z (the lines representing bonds in this instance) and —X and -Z are as hereinbefore defined.

In formula (IA) $Y_1$ can be any of the linking groups listed above for the moiety linking X and Z but is preferably a straight or branched chain alkyl linking group containing from 1 to 20 carbon atoms and preferably from 2 to 10 carbon atoms; or is phenyl, naphthyl, cyclopentyl or cyclohexyl; or when Z is an oxyethylene or an oxyethylene-containing polymer, $Y_1$ preferably represents a direct link between X and Z.

Structure (IA), wherein Z is an oxyethylene containing polymer thus has the formula,

wherein $R_4$, r and s are as defined in relation to formula (VI) above. When -Z is a block copolymer, structure (IA) has the formula

wherein $R_{4'}$, r', s' and t are as defined in relation to formula (VII) above. An example of a compound of formula (IA) wherein X is —OH is methoxy-polyethylene glycol of molecular weights from 350 to 2000 [MeO(EO)$_n$OH]. A further example of a compound of formula (IA) wherein X is amino is JEFFAMINE XTJ-508 [MeO(EO)$_n$(PO)$_m$NH$_2$] wherein n is 32 and m is 10. The molecular weight is 2000. (JEFFAMINE is a trademark of Huntsman).

Examples of compounds of formula (IA) in which $Y_1$ is an alkyl linking group include taurine sodium salt [H$_2$NCH$_2$CH$_2$SO$_3$Na], 2-mercaptoethanesulphonic acid [HSCH$_2$CH$_2$SO$_3$H], 2-(dimethylamino)-ethanethiol hydrochloride [(CH$_3$)$_2$N$^+$(H)CH$_2$CH$_2$SH] Cl$^-$ and 3-mercaptopropionic acid [HSCH$_2$CH$_2$CO$_2$H] and salts thereof.

When Y$_1$ is a ring structure group such as an aryl group, the substituents X and Z in formula (IA) may be direct substituents in the ring for example:

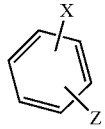

(ID)

If X and Z are adjacent substituents capable of reacting together such as carboxyate and/or sulphonate they may form a cyclic anhydride capable of ring-opening under the reaction conditions. An example of such a compound is 2-sulphobenzoic acid anhydride.

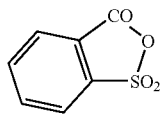

In structure (II) where two groups X are at distal ends of the molecule, -Z- may be an oxyethylene containing polymer and there is a direct bond between -Z- and each —X. Thus one preferred structure (II) has the formula:

X—(EO)$_a$(PO)$_b$—X'      (IIA)

wherein a and b are independently from 0 to 3000 or more preferably from 0 to 2000, provided that a is not 0 and the total of a+b is from about 7 to about 3000 or more preferably from about 10 to about 2000 and EO and PO represent oxyethylene and oxypropylene respectively which may be arranged in random or block formation. More preferably, a and b are independently from 0 to 200, provided that the total of a+b is from about 10 to about 200. Preferably a is greater than b, for example it is preferred that a is at least 4 times greater than b. When -Z- represents an ethylene oxide, propylene oxide block copolymer, the compound may have the structure X—(PO)$_a$—(EO)$_b$—(PO)$_c$—X'      (IIB)

wherein a', b' and c are independently from 0 to 2000, provided that b' is not 0 and the total of a'+b'+c is from about 7 to about 3000 or more preferably from about 10 to about 2000 and EO and PO represent oxyethylene and oxypropylene respectively. Preferably b' is greater than the sum of a'+c, for example at least 4 times greater than the sum of a'+c. Preferably a', b' and c are independently from 0 to 200, provided that the total of a'+b'+c is from about 10 to about 200. The groups X and X' may be the same or different but are conveniently the same. An example of a compound of formula (IIB) wherein the terminal —OH groups are replaced by —NH$_2$ is JEFFAMINE ED2003 [H$_2$NCHMeCH$_2$—(PO)$_a$—(EO)$_b$—(PO)$_c$—NH$_2$], where a+c=2.5 and b=41, available from Huntsman.

Alternatively -Z- in structure (II) may be quaternary ammonium. Thus for example a further preferred structure (II) has the formula (IIC)

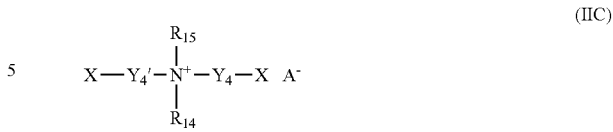

wherein R$_{14}$ and R$_{15}$, which may be the same or different are hydrogen C$_1$ to C$_{20}$ straight or branched chain alkyl; aryl for example phenyl; or C$_1$ to C$_4$ aralkyl, for example benzyl, wherein each aryl group may be optionally substituted by conventional substituents such as C$_1$ to C$_4$ alkyl, nitro and halo and wherein Y$_4$ and Y$_{4'}$ which may be the same or different are

—R$_8$—

—R$_7$-(L$_1$)$_n$- wherein R$_7$, and R$_8$ are independently C$_1$ to C$_{10}$ straight or branched chain alkyl linking groups optionally substituted by halogen or ether, for example C$_1$ to C$_4$ alkoxy and (L$_1$)$_n$ is a polyoxyalkyene group such as polyoxyethylene or more preferably polyoxypropylene or polyoxybutylene; n is from 2 to 20, preferably from 4 to 10 and A— is a suitable anion.

It is preferred that both R$_{14}$ and R$_{15}$ are not hydrogen at the same time. An example of a surface modifying compound of formula (IIC) is a benzoxonium chloride such as that illustrated below or an amino oxyethylene diol such as that illustrated below.

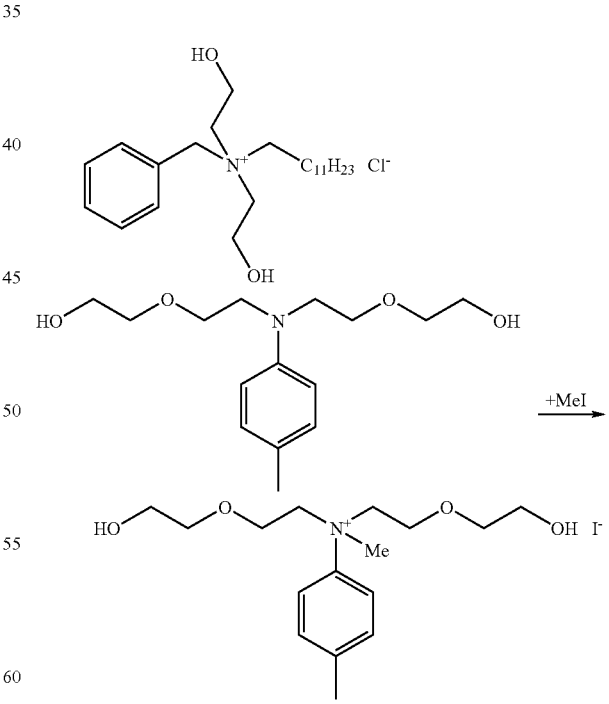

Structure (III), where two X groups are at distal ends of the molecule and Z is a pendant group, may in one embodiment take the form:

X—Y$_2$—C(Z)(R$_6$)—Y$_2$'—X'      (IIIA)

wherein $R_6$ is hydrogen or more preferably a $C_1$ to $C_4$ alkyl group optionally substituted by ether, for example $C_1$ to $C_4$ alkoxy or halogen and $Y_2$ and $Y_2'$, which may be same or different are independently —$R_7$-$(L_1)_n$- or

—$R_8$— wherein $R_7$, and $R_8$ are independently $C_1$ to $C_{10}$ straight or branched chain alkyl linking groups optionally substituted by halogen or ether, for example $C_1$ to $C_4$ alkoxy and $(L_1)_n$ is a polyoxyalkyene group such as polyoxyethylene or more preferably polyoxypropylene or polyoxybutylene; n is from 2 to 20, preferably from 4 to 10.

Compounds of formula (IIIA) are illustrated by (i) the propoxylated derivative of 1,4-butanediol-3-sodiosulphonate (ii) dimethylolpropionic acid ("DMPA") and (iii) dimethylol butyric acid ("DMBA").

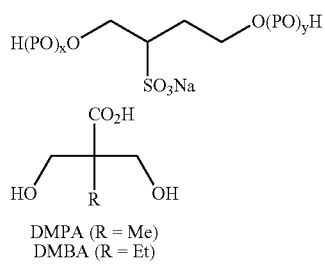

DMPA (R = Me)
DMBA (R = Et)

When the moiety linking X and Z is a ring structure group such as an aryl group, the substituents X and Z in formula (III) may be direct substituents in the ring for example:

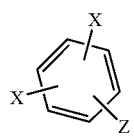

(IIIB)

An example of a compound of structure (IIIB) is illustrated by esters of 5-sodiosulphoisophthalate (SSIPA) where the groups $R_5$, which may be the same or different, are a hydrocarbyl moiety having 1-30 carbon atoms optionally linked or substituted by one or more halo, amino, ether or thioether groups or combinations of these. Preferably $R_5$ is a $C_6$ to $C_{20}$ straight or branched chain alkyl group.

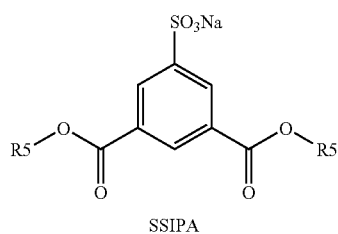

SSIPA

Alternatively the groups X and Z may be joined to the ring structure via linking groups, for example the compound of structure (III) may have the formula (IIC):

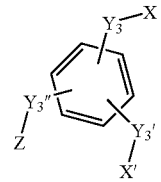

IIIC wherein $Y_3$, $Y_3'$ and $Y_3''$ may individually represent a direct link between X, X' or Z (as the case may be) and the ring structure or may represent one of the linking groups described above. In particular, $Y_3$, $Y_3'$ and $Y_3''$ may independently have the definitions for $Y_2$ given above.

Alternatively $Y_3$, $Y_3'$ and $Y_3''$ may independently be a group -$(L_2)$-$R_9$ where $L_2$ is an ester linking group —C(O)—O, $R_9$ is an oxyethylene, oxypropylene or oxybutylene group or polyoxyethylene, polyoxypropylene or polyoxybutylene group having a degree of polymerisation from 2 to 20. In one embodiment $Y_3''$ represents a direct link between Z and the aryl ring and —$Y_3$— and —$Y_3'$— are both -$(L_2)$- $R_9$— as herein defined wherein $R_9$ is oxyethylene and X is —OH. An example of a compound of formula IIIC is (iv) bis(2-hydroxyethyl)-5-soidiosulphoisophthalate ("EG-SSIPA").

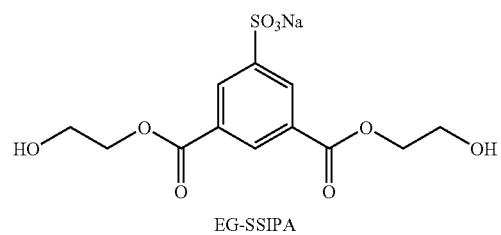

EG-SSIPA

A further preferred class of compound of structure III has the formula IID:

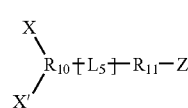

IIID wherein $R_{10}$ is a $C_1$ to $C_8$ straight or branched chain alkyl group and the two groups X and X', which may be the same or different, may be attached to the same carbon atom in the alkyl chain or to different carbon atoms in the alkyl chain, -$L_5$- is a linking group which is -$(L_1)_n$- or

—$R_8$— wherein $R_8$, and $(L_1)_n$ are as defined above in relation to formula (IIIA) and $R_{11}$ is $C_1$ to $C_4$ alkyl. As an example of a compound of formula (IIID), there may be mentioned Tegomer DS3117, a sulphonated diol supplied by Goldschmidt.

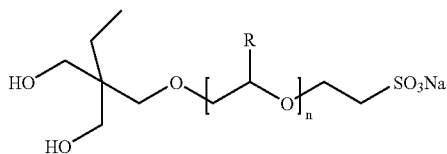

Tegomer DS3117 n = 20 to 25; R = H or CH$_3$

In structure (IV), the group —X— is both a linking group and is capable of reacting with the wall-forming material. It is preferred that the group —X— in structure (IV) is —NH—. Thus a general formula for a compound of structure (IV) is (IVA):

wherein Y and Y' may be any of the linking moieties described above or, when Z is an oxyethylene containing polymer may represent a direct link betveen Z- and —NH—. It will be appreciated that the reactivity of the groups —X and —NH— respectively with the wall-forming material will not necessarily be the same and, depending on the groups concerned, the primary reaction with the wall-forming material may be either via the terminal group —X or via the group —NH—. In some circumstances there may be no reaction between a group —NH— and the wall-forming material and in such a case, the group —NH— should not be regarded as a group —X— but rather as an internal amino linking group in the moiety joining X and Z. Preferred structures of Y and Y' include independently a straight or branched chain $C_1$ to $C_{10}$ alkyl group, a polyoxyethylene, or more preferably polyoxypropylene or polyoxybutylene polymer chain of formula -($L_1$)$_n$- as defined above or a group -($L_2$)-$R_9$— as defined above or a group —$R_{12}$-($L_2$)-$R_9$— wherein $R_9$ and $L_2$ are as defined above and $R_{12}$ is a $C_1$ to $C_4$ alkyl group. Compounds of formula (IVA) are represented for example by

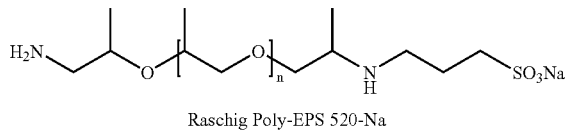

Raschig Poly-EPS 520-Na (i) PolyEPS 520 available from Raschig wherein —Y— is polyoxyproplyene and Y' is a $C_3$ alkyl group, (ii) the Michael adduct of Jeffamine 1000M (available from Huntsman) and ethylhydroxyethylacrylate wherein Z is a methyl-capped polyoxyethylene-containing polymer linked directly to —NH— and Y' is a group —$R_{12}$-($L_2$)-$R_9$— as defined above in which $R_9$ is oxyethylene [MeOEO$_n$PO$_m$NHCH$_2$CH$_2$COOCH$_2$CH$_2$OH where n is about 18 and m is about 3] (iii) the ethoxylated adduct of Jeffamine M1000 wherein Z is a methyl-capped polyoxyethylene-containing polymer linked directly to —NH— and Y is a polyoxyethylene group [MeOEO$_n$PO$_m$NH(CH$_2$CH$_2$O)$_n$H].

Structure (V) is illustrated by the sulfonate polyester polyol prepared by reacting sodium sulphoisophthalic acid, adipic acid, cyclohexane dimethanol, methoxy-polyethylene glycol (MW 750) and trimethylol propane to give a product having a hydoxyl number in the range of from 150 to 170.

There may be a variation in the structural composition of the product depending on the conditions used. It will be appreciated by those skilled in the art that the reaction will produce a complex mixture of molecules and the structure (V) should not therefore be taken as an exact representation of the sulphonate polyester polyol. Typically however the sulphonate polyester polyol will have at least two terminal —OH groups whilst the sulphonate group provides the -Z group. Structural variations however may mean that the number of moieties —X are average rather than absolute or an exact integer and in particular on average there may not be exactly three —X groups.

The wall forming material may be any wall-forming monomer, oligomer or pre-polymer conventionally used in microcapsule wall-formation. Examples include a wide variety of isocyanate polymerisation precursors, non-isocyanate precursors and optionally etherified urea-fonmaldehyde prepolymers. Examples of non-isocyanate precursors include precursors for polyester polythioester and polyamide (wherein the wall-forming moiety which reacts with the group(s) —X is —COCl), polysulfonamide (wherein the wall-fonming moiety which reacts with the group(s) —X is —SO$_2$Cl), polyphosphonamide (wherein the wall-forming moiety which reacts with the group(s) —X is —POCl$_2$), polycarbonate (wherein the wall-forming moiety which reacts with the group(s) —X is —OCOCl) and polysiloxane (wherein the wall-forming moiety which reacts with the group(s) —X is SiRR'Cl).

It is preferred however that the wall-forming material is an isocyanate wall-forming material wherein the wall-fonming moiety which reacts with the groups(s) —X is isocyanate or an optionally etherified urea-formaldehyde prepolymer wherein the wall-fonming moiety which reacts with the groups(s) —X is methylol or etherified methylol.

Isocyanates suitable for conventional wall-forming processes for microcapsules will be familiar to those skilled in the art and may be used in the process of the present invention. Furthermore since wall-formation per se is not required in the present invention certain monofunctional isocyanates may be used which find only limited use in conventional microencapsulation.

Thus suitable isocyanates include, inter alia, aromatic isocyanates such as isomers of tolylene diisocyanate, isomers and derivatives of phenylene diisocyanate, isomers and derivatives of biphenylene diisocyanates, polymethylenepolyphenyleneisocyanates (PMPPI), aliphatic acyclic isocyanates such as hexamethylene diisoocyanate (HMDI), cyclic aliphatic isocyanates such as isophoronediisocyanate (IPDI) and trimers of HMDI. Moreover, monofunctional isocyanates such as p-tolyl isocyanate, alkyl isocyanates such as dodecyl isocyanate or hexadecyl isocyanate can be successfully employed in these systems to produce surface-bound surfactants by the hereinbefore described interfacial reaction. Chain extended isocyanates such as those obtained by alkylene glycol partial urethane reactions can also be employed to good effect in this process. Mixtures of isocyanates may be used.

The surface modifying compounds of the present invention contain one or more functional groups (designated as —X) capable of reacting with wall forming material, in this instance with isocyanate. The reactions of the moiety X with isocyanates are illustrated herein below using structure (IA) for simplicity although the reactions of the remaining structures correspond accordingly. For example, carboxylic acids react with isocyanates to form mixed anhydrides that rapidly eliminate carbon dioxide with the formation of carboxylic amides:

$$RNCO+Z\text{-}Y\text{—}CO_2H \rightarrow [RNHCOOCO\text{—}Y\text{-}Z^1] \rightarrow Z\text{-}Y\text{—}CONHR+CO_2$$

Thiol, hydroxyl and amino groups react with isocyanates to form respectively thiocarbamate, urethane, and urea linkages:

$$RNCO+Z\text{-}Y\text{—}SH \rightarrow RNHCO\text{—}S\text{—}Y\text{-}Z \text{ thiocarbamate linkage}$$

$$RNCO+Z\text{-}Y\text{—}OH \rightarrow RNHCO\text{—}O\text{—}Y\text{-}Z \text{ urethane linkage}$$

$$RNCO+Z\text{-}Y\text{—}NHA \rightarrow RNH\text{—}CO\text{—}NA\text{—}Y\text{-}Z \text{ urea linkage}$$

While any functional group of the above types may be used to introduce surface modifying compounds into the microcapsule walls of the present invention, hydroxyl and amino groups are particularly preferred unless a slower reaction is desired as discussed below. The preferred groups are chosen on the basis of the process and on the desired properties of the interfacial surfactant layer as is discussed in greater detail below.

The reactivity of the functional group with the isocyanate influences the process of choice. For example, the reaction with amines is very fast, allowing modification from an interfacial modifying compound in the aqueous phase with wall-forming materials in the oil phase. In contrast, the reaction with alcohols or thiols is much slower and may permit hydrolysis of the isocyanate with the possibility of consequent wall formation if introduced from the aqueous phase. Reaction of isocyanates with these molecules is thus more readily accomplished in the oil phase.

As indicated previously, substantially all of the polymer-forming moieties in the monomer, oligomer or pre-polymer are reacted with a reactive moiety on the interface modifying compound such that a surfactant is formed and little or no wall-forming functionality remains after reaction. In general therefore the stoichiometry of the reaction of the interface modifying compound and the isocyanate group of the wall-forming material is substantially 1:1, that is to say for each wall-forming isocyanate moiety present in the wall-forming material there is a corresponding reactive group —X in the interface modifying compound. An excess of interface modifying compound may be used if desired but there is no particular advantage in doing so. Similarly, in the non-isocyanate systems, it is preferred that the stoichiometry of the reaction of the interface modifying compound and the wall-forming group is substantially 1:1, that is to say for each wall-forming moiety present in the wall-forming material there is a corresponding reactive group —X in the interface modifying compound.

It will be appreciated that in some circumstances (and in particular when a microcapsule wall may be formed by the action of water on the wall-forming isocyanate or by self-condensation) there may be a competition between (a) the reaction of the interface modifying compound and the wall-forming material and (b) a wall-forming reaction of the wall-forming material. For example as discussed above, if a slow reacting interface modifying compound is added through the aqueous phase, significant hydrolysis of the isocyanate and some consequent wall formation may take place before all the isocyanate groups have been reacted with the interface modifying compound. Reaction conditions are preferably chosen such that the reaction of the interface modifying compound and the wall-forming material predominates. For example if wall forming reactions conventionally take place at elevated temperature, the reaction with the interface modifying compound is suitably conducted at a lower temperature, such as ambient temperature, using an interface modifying compound capable of reacting at the lower temperature.

Emulsions in which a minor proportion of wall formation has taken place in competition with the reaction of the isocyanate (or other wall-forming moiety in the alternative systems) and the interface modifying compound are not however excluded from the present invention. In general the weight ratio of the surfactant/wall layer to the total emulsion droplet/microcapsule, whilst not being a direct measure, is highly indicative of the degree of wall formation. It will generally be the case that the weight ratio of the surfactant/wall layer to the total droplet/microcapsule (surfactant/wall layer plus content of the droplet/microcapsule) is less than 1% by weight.

Where more than two functional groups (—X) are present, it is possible to generate cross-linking reactions. For example when two functional groups (—X) are present, reaction with a difunctional isocyanate will result in a linear chain-extended interface modified molecule.

Catalysts may be used to promote reaction between isocyanates and the interface modifying compound, particularly when the group (—X) or the isocyanate is relatively unreactive. When such reaction is accomplished in a homogeneous oil phase, catalysts such as dibutyltin dilaurate are suitable. When such reaction is accomplished at the interface of an oil-in-water emulsion, phase transfer catalysts such as those described in U.S. Pat. No. 4,140,516 are suitable.

Preferred wall-forming materials utilized in forming the emulsions of this invention also include optionally etherified urea-formaldehyde resins, (urea-formaldehyde prepolymers). Preferably they are etherified and comprise urea-formaldehyde prepolymers or resins in which the methylol (—CH$_2$OH) groups have been etherified by reaction with an alcohol, preferably a C$_4$-C$_{10}$ alkanol, most preferably n-butanol. Preferably from about 50 to about 98%, and most preferably from about 70 to about 95%, of the methylol groups in the prepolymer have been etherified.

Etherified urea-formaldehyde prepolymers suitable for use in the invention include those available, for instance, under the Beetle trademark from American Cyanamid, the Resimene trademark from Solutia, and the Beckamine trademark from Reichold Chemicals.

In terms of the aminoplast system, the interface-modifying agents of the present invention contain one or more functional groups (designated as —X) capable of reacting with methylol and etherified methylol groups. Their reactions with the wall-forming urea formaldehyde prepolymers are illustrated below using structure (IA) for simplicity although the reactions of the remaining structures correspond accordingly.

For example, hydroxyl groups of a surface-modifying agent are believed to react with methylol or ether groups in the prepolymer to form ether linkages:

$$>NCH_2OR+HO\text{—}Y\text{-}Z \text{ U}>NCH_2\text{—}O\text{—}Y\text{-}Z+ROH$$

where R is hydrogen (forming a methylol group) or (C$_4$-C$_{10}$) alkyl (forming an ether group). Note, however, that under certain conditions this reaction may be reversible and the product containing a new ether linkage NH$_2$—O—R'-Z may not be sufficiently stable under the process conditions.

Amino groups in a surface-modifying agent are believed to react with methylol or ether groups in the prepolymer to form amino linkages:

where A is hydrogen or $C_1$-$C_4$ alkyl. This reaction is expected to be less reversible than the above ether-producing reaction, and the products more stable.

Thiol groups in a surface-modifying agent are believed to react with the methylol or ether groups in the prepolymer to form thioether linkages:

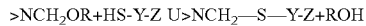

This reaction is expected to be less reversible than the above ether producing reaction and the products more stable. In general therefore it is preferred that —X is an amino or in particular a thiol group when an aminoplast system is used.

The reactivity of the functional group in the interface-modifying agent with the prepolymer influences the choice of process as well as of the surface-modifying compound. For example, the reaction with thiols is less reversible than that with alcohols, allowing modification from an agent in the aqueous phase with wall-forming materials in the oil phase.

As with the isocyanate systems discussed above, it is preferred that the stoichiometry of the reaction of the interface modifying compound and the methylol (or ether group) of the wall-forming material is substantially 1:1, that is to say for each wall-forming methylol or ether moiety present in the wall-forming material there is a corresponding reactive group —X in the interface modifying compound.

It will be appreciated however that for a complex urea-formaldehyde pre-polymer it may not be practicable to react every wall-forming methylol or ether moiety present in the wall-forming material with a corresponding reactive group —X and that any remaining methylol or ether moieties are unlikely to take part in wall-forming reactions. Indeed if the emulsion of the present invention is never subjected to wall-forming conditions (for example in the case of urea-formaldehyde resins, heat and pH adjustment), potential wall-forming moieties may remain so long as such conditions are not applied. Thus whilst substantially all of the wall-forming moieties of the wall-forming material should reacted with one or more groups —X of the interface modifying compound such that little or no wall-forming functionality remains after reaction, the situation in which wall forming conditions are never applied to the emulsion is regarded as one in which no wall-forming functionality remains after reaction of the wall-forming material and the interface modifying compound and furthermore that unreacted moieties such as methylol or ether moieties of urea formaldehyde prepolymers are not to be regarded as wall-forming moieties unless and until wall-forming conditions are applied to the emulsion.

The nature of the material to be emulsified is not critical to the scope of the present invention and any material suitable for emulsification as a dispersed phase may be used. The benefits of the present invention may however be of particular relevance to specific dispersed phase materials and applications. For example the emulsion of the present invention will find particular utility in applications for which emulsion stability, aggregation and re-disperasability tend to present problems. The dispersed material is typically a liquid and, in the case of agricultural products, may be comprised of one or more pesticides, or, in the case of non-agricultural products, may be comprised of inks, dyes, biological actives, pharmaceuticals or other products. For agricultural products, the dispersed phase may be an organic solution, typically immiscible with water, comprising one or more pesticides as the active ingredient, including insecticides, herbicides, fungicides and biocides. The pesticide may be a liquid, a solid pesticide that has been dissolved in a solvent that is immiscible with water, or a solid suspended in the organic solution that may have within it another pesticide. The organic solution may also have an photostabilising protectant suspended or dissolved within it.

Any agrochemical which is suitable for emulsification may be used, but by way of illustration only, examples of suitable herbicides are s-triazines, e.g., atrazine, simazine, propazine, cyprozine; Sulphonylureas e.g., chlorsulfuron, chlorimuronethyl, metsulfuron-methyl, thiameturon-methyl; foramsulfuron, Iodosulforn and Triketones e.g., sulcotrione. Another suitable compound is the fungicide (E)methyl-2-[2-(6-(2-cyanophenoxy)pyrimidin-4-yloxy)phenyl]-3-methoxypropenoate.

Examples of suitable insecticides include permethrin, cypermethrin, deltamethrin, fenvalerate, cyfluthrin, resmethrin, allethrin, etofenprox tefluthrin and lambda-cyhalothrin.

The liquid in which the solid is suspended may suitably be a second herbicide, especially a thiocarbamate or a haloacetanilide, and preferably acetochlor. The haloacetanilides, particularly the subclass generally known as a-chloroacetanilides, are a well-known class of herbicidal agents and have been used and proposed for use in a number of crop and non-crop applications. Some of the better known members of this class include α-chloro-6'-ethyl-N-(2-methoxy-1-methylethyl)-acetanilide (metolachlor), N-butoxymethyl-α-chloro-2',6'-diethylacetanilide (butachlor), α-chloro-2',6'-diethyl-N-methoxymethylacetanilide (alachlor), 2-chloro-N-(ethoxymethyl)-6'-ethyl-o-acetotoluidide (acetochlor) and α-chloro-N-isopropylacetanilide (propachlor). Many other compounds of this type are disclosed in numerous patents.

The thiocarbamates are a well known class of herbicide which includes Molinate (S-ethyl hexahydro-1H-azepine-1-carbothioate); Butylate (S-ethyl diisobutylthiocarbamate); EPTC (ethyl dipropylthiolcarbamate); Triallate (2,3,3-trichloroallyl-diisopropylthiolcarbamate); Diallate (cis-1-trans-2,3-dichloroallyl-diisopropylthiolcarbamate); and Vemolate (S-propyl dipropylthiolcarbamate). When the liquid is an herbicide, the microcapsules of the invention suitably contain 0.1-55% by weight of biologically active compounds.

The liquid may alternatively be any organic solvent that is immiscible with water, and is polar enough to dissolve the monomers, oligomers or prepolymers used to form the walls of the microcapsules. Suitable solvents are well known to those skilled in the art. By way of illustration, examples of such solvents are aromatic compounds such as xylenes or naphthalenes, especially Solvesso 200; aliphatic compounds such as aliphatic or cycloaliphatic hydrocarbons, for example hexane, heptane and cyclohexane; alkyl esters such as alkyl acetates for example Exxate 700 or Exxate 1000 and such as alkyl phthalates for example diethyl phthalate and dibutylphthalate; ketones such as cyclohexanone or acetophenone; chlorinated hydrocarbons; alcohols, such as isopropyl alcohol; and vegetable oils. The solvent may be a mixture of two or more of the above solvents. A safener for either herbicide may be present, and many such safeners or antidotes are well known in the art. Preferred types for use with haloacetanilide herbicides include dichloroacetamides such as dichlormid (N,N-diallyl dichloroacetamide);2,2,5- trimethyl-3-dichloroacetyl oxazolidine (R-29148), N-dichloroacetyl-1-oxa-4-azaspiro[4,5]decane (AD-67);4-dichloroacetyl-2,3-dihydro-3-methyl-1,4-benzoxazine (CGA-154281);1-(dichloroacetyl)hexahydro-3,3,8a-trimethylpyrrolo-[1,2-a]-p-yrimidin-6(2H)-one and N-(1,3-dioxolan-2-yl-methyl)-N-(2-propenyl)-2,2-dichloroacetamide (PPG-1292). These and other dichioroacetamides are described, for instance, in U.S. Pat. Nos. 4,124,372; 4,256,481; 4,294,764; 4,448,960; 4,601,745; 4,618,361; 4,708,735 and 4,900,350. Additional known types of safeners or antidotes include certain oxime derivatives (U.S. Pat. Nos. 4,070,389 and 4,269,775, for instance), thiazole carboxylic acids and derivatives (U.S. Pat. No. 4,199,506 for instance), haloacyltetrahydroisoquinolines (U.S. Pat. No. 4,755,218, for example), aryl cyclopropane carbonitriles (U.S. Pat. No. 4,859,232, for example) and 1,8-naphthalic acid, its anhydride and derivatives. Safeners or antidotes, when included, will usually be contained in the organic or water-immiscible phase.

When a photostabilising protectant is used in this invention, it is preferably titanium dioxide, zinc oxide, or a mixture of titanium dioxide and zinc oxide. In general, the photostabilising protectant is used in an amount of from about 0.1 to about 50 weight %, preferably from about 1 to about 10 weight %, with respect to the organic phase. Mixtures of titanium dioxide and zinc oxide will contain these two substances in a weight ratio of from about 1:10 to about 10:1.

Biologically active materials suitable for the present invention that are subject to degradation or decomposition by ultraviolet light and therefore requiring a protectant include the pyrethroids and pyrethrins. Many of the pyretioids known to be susceptible to degradation by ultraviolet light include permethrin, cypennethrin, deltamethrin, fenvalerate, cyfluthrin, resmethrin, allethrin, etofenprox, and lambda-cyhalothrin. Other biologically active materials that are known to be susceptible to degradation or decomposition by ultraviolet light include the herbicides trinfluralin, ioxynil and napropamide, the insecticides pirimiphos-methyl and chlorpyrifos and the fungicide azoxystrobin. Microcapsules of this invention may contain two or more ultraviolet light sensitive biologically active materials.

The liquid utilized in this invention may be a liquid biologically active material which itself is susceptible to degradation by ultraviolet light, or a biologically active material which is not normally so susceptible (but in which there is suspended a second biologically active material which is light-sensitive), or an organic solvent which is immiscible in water and in which the ultraviolet light sensitive material is suspended or dissolved. The liquid, in any case, should be sufficiently polar to dissolve the prepolymer or prepolymers used to form the microcapsule wall.

Emulsions of the present invention may also be transformed into suspoemulsions containing at least two materials which are dissolved or supended in the aqueous phase (or both aqueous phases) of the suspension. Such combination products are storage stable and enable, for example, the production of a combination pesticidal product wherein incompatible pesticides may be applied together.

Those skilled in the art will be readily able to apply conventional processes for the preparation of emulsions according to the invention in non-agrochemical fields including but not limited to encapsulated dyes, inks, pharmaceuticals, flavouring agents and fragrances. Oil-in-water techniques are generally more suitable although the present invention also includes water-in-oil emulsion techniques.

Conventional solvents may be used for the oil phase such as those described above in connection with microcapsules for agrochemical use.

The reaction of the interface modifying compound and the wall-forming material may take place in an organic phase as a pre-reaction. The resultant surfactant may be isolated or may be used in solution in the organic phase, for example the oil phase containing the surfactant product may subsequently be emulsified into water. If desired the course of the reaction may be monitored, for example by infra-red detection of the isocyanate group, to ensure that all isocyanate groups are fully reacted. Any material, such as an agrochemical, to be contained in the dispersed phase may be added to the organic phase either before or, preferably, after the reaction of the interface modifying compound and wall forming material has taken place.

Alternatively, the interface modifying compound and the wall-forming material may be reacted in an organic phase after emulsification has taken place.

Alternatively the wall-forming material may be dissolved in an oil phase which is dispersed in water (optionally in the presence of additional surfactants and optionally in the presence of any material, such as an agrochemical, to be contained in the dispersed oil phase) whilst the interface modifying compound is added to the aqueous continuous phase. Thereafter the interface modifying compound and the wall-forming material react at the interface of the continuous phase and the dispersed phase droplets to form the surfactant.

Exemplification of Emulsion Formation

List of raw materials employed in examples:

Solvesso 200 (from Exxon)

Solvesso 100 (from Exxon)

Methyl Oleate (from Cognis)

Suprasec 2211 (commercial grade of PAPI)

Suprasec 5025 (commercial grade of PAPI)

tolyl di-isocyanate (from Aldrich)

Tolyl isocyanate (from Aldrich)

Dodecyl isocyanate (from Aldrich)

Jeffamine M-1000 (Alkoxylated amine from Huntsman Chemicals)

Jeffamine M-2070 (Alkoxylated amine from Huntsman Chemicals)

Hyvis 07 (commercial polyisobutene from BP Chemicals)

Jayflex DINP (di-isononyl phthalate from Exxon)

Poly EPS-520 Na (as in patent text from Raschig)

Lambda cyhalothrin (insecticide from Syngenta)

fluazifop-p-butyl (herbicide from Syngenta)

picoxystrobin (fungicide from Syngenta)

1. Isocyanate—PEG-Me Surfactants

Emulsions were made by adding oil (eg Solvesso containing the reacted components to produce a surfactant) to water and shearing to produce an emulsion.

Surfactants were made by stirring at room temperature a solution of the oil phase (either solvesso 200 or methyl oleate as stated in Table 1) containing a suitable isocyanate (2% by weight of oil phase) and a suitable methyl capped PEG (polyethyelene glycol) (1 mole equivalent relative to the isocyanate). The time taken for the two components to react was dependent on the nature of the isocyanate. In each case 10 g of the emulsion was produced with an internal phase of 50% by weight of the EW. The oil phase was added to water under low shear (800 rpm) using an Ystral X1020 mixer before being high shear mixed (3000 rpm) for 2 minutes to produce the emulsion.

COMPARATIVE EXAMPLES (a) Solvesso 200 (Commercial aromatic solvent from Exxon)

(b) Suprasec 2211 (PAPI commercial grade from Huntsman chemicals) & Solvesso 200

(c) PEG-Me 350 (available from Aldrich) & Solvesso 200

(d) PEG-Me 550 (available from Aldrich) in methyl oleate

The reactive components were added in each of the above comparative examples at 2% by weight relative to the oil phase. These oil phases were added to water and emulsification attempted but all products were highly unstable.

The remaining examples illustrate the reaction of an isocyanate with a methyl capped PEG (of varying molecular weight) to produce in-situ surfactants (as illustrated by their ability to emulsify the oil on addition to water).

The reacted components all produced good quality emulsions. The comparative examples all failed to emulsify the oil when added to water.

2. Isocyanate-Amine Interfacially Produced Surfactants

Emulsions were produced by dissolving an isocyanate (2% by weight of oil phase) in the oil and adding this to water containing a mole equivalent of the amine to allow a surfactant to be produced at the interface of the developing emulsion as the mixture is sheared. In each case 10 g of the emulsion was produced with an internal phase of 50% by weight of the EW (unless stated otherwise). The oil phase was added to the water under low shear using an Ultra Turrax mixer before high shear mixing at the mixer's maximum shear rate for 1 minute to produce the final emulsion. The volume mean diameter $\{D(v, 05)\}$ of the resulting emulsions were measured using a Malvern Mastersizer. Longer term stability b was assessed by evaluating the emulsions (where stated) after one month storage at ambient temperature.

COMPARATIVE EXAMPLES (a) Jeffamine M-1000 (in aqueous phase) with Solvesso 200
(b) Jeffamine M-2070 (in aqueous phase) with Solvesso 200
(c) Jeffamine D-400 (in aqueous phase) with Methyl oleate
(d) Jeffamine M-2070 (in aqueous phase) with methyl oleate
(e) Jeffamine M-2070 (in aqueous phase) with Hyvis 07(5% relative) dissolved in Solvesso 200 (to establish emulsification in an "Ostwald Ripening Inhibited" situation)
(f) Jeffamine D-400 (in aqueous phase) with DNIP

TABLE 1

| PEG-Me | solvent | Isocyanate | Hours stirring | % w/w oil phase | Initial emulsion formed | Longer term stability | Droplet size/ μD(v, 0.5) |
|---|---|---|---|---|---|---|---|
| Comparative example (a) | Solvesso 200 | — | 0 | 50 | no | — | — |
| 350 (Comparative example (c)) | Solvesso 200 | — | 0 | 50 | no | — | — |
| Comparative example (b) | Solvesso 200 | Suprasec 2211 | 0 | 50 | no | — | — |
| 350 | Solvesso 200 | Suprasec 2211 | 24 | 50 | yes | yes | 1.59 |
| 550 | Solvesso 200 | Suprasec 2211 | 20 | 50 | yes | yes | 1.31 |
| 750 | Solvesso 200 | Suprasec 2211 | 20 | 50 | yes | yes | 1.09 |
| 350 | Solvesso 200 | tolyl di-isocyanate | 65 | 50 | yes | yes | 22.51 |
| 550 | Solvesso 200 | tolyl di-isocyanate | 65 | 50 | yes | yes | 1.21 |
| 750 | Solvesso 200 | tolyl di-isocyanate | 65 | 50 | yes | yes | 1.03 |
| 550 (comparative example (d)) | methyl oleate | — | — | 50 | no | — | — |
| 350 | methyl oleate | Suprasec 2211 | 48 | 50 | yes | creaming | 2.63 |
| 550 | methyl oleate | Suprasec 2211 | 24 | 50 | yes | creaming | 2.35 |
| 550 | methyl oleate | tolyl di-isocyanate | 48? | 50 | yes | creaming | 1.82 |

| Amine | Oil phase | Isocyanate | % oil phase | Initial emulsion formed? | Longer term stability? | D(v, 0.5)/ microns |
|---|---|---|---|---|---|---|
| Jeffamine M1000 | Solvesso 200 | Suprasec 2211 | 50 | yes | yes | 5.21 |
| Jeffamine M1000 Comparative Example (a) | Solvesso 200 | none | 50 | yes | no | >50. Classed as did not emulsify |
| Jeffamine M2070 | Solvesso 200 | Suprasec 2211 | 50 | yes | yes | 6.20 |
| Jeffamine M2070 Comparative Example (b) | Solvesso 200 | none | 50 | no | no | — |
| Jeffamine M2070 | Methyl oleate | Tolyl di-isocyanate | 50 | yes | yes | 1.95 |
| Jeffamine M2070 | Solvesso 200 | Dodecyl isocyanate | 50 | yes | yes | 5.30 |
| Jeffamine M2070 | Methyl oleate | Dodecyl isocyanate | 50 | yes | yes | 2.46 |
| Jeffamine M2070 | Solvesso 200 | p-Tolyl isocyanate | 50 | yes | yes | 4.48 |
| Jeffamine M2070 | Methyl oleate | p-Tolyl isocyanate | 50 | yes | yes | 2.09 |
| Jeffamine M2070 Comparative Example (d) | Methyl oleate | none | 50 | Yes | Yes | 1.88 |
| Jeffamine D400 Comparative Example (c) | Methyl oleate | none | 50 | yes | yes | 3.03 |
| Jeffamine D400 Comparative Example (f) | Jayflex DINP | none | 50 | No | No | — |
| Jeffamine M2070 | Jayflex DINP | Suprasec 2211 | 50 | yes | yes | 1.08 |
| Jeffamine M2070 Comparative Example (d) | Jayflex DINP | none | 50 | yes | yes | 2.49 |
| Jeffamine M2070 Comparative Example (e) | 19:1 Solvesso 200: Hyvis 07 | none | 50 | yes | yes | 1.90 |
| Poly EPS-520 Na (1 mole equiv) | Solvesso 200 | p-Tolyl isocyanate | 50 | yes | Not tested | 20 |
| Poly EPS-520 Na (2 mole equivs) | Solvesso 200 | p-Tolyl isocyanate | 50 | yes | Not tested | 3.5 |
| Jeffamine M-1000 | Lambda-cyhalothrin (75% w/w in Solvesso 100) | p-Tolyl isocyanate | 50 | Yes | Not tested | 2.7 |
| Jeffamine M-1000 | Lambda-cyhalothrin (75% w/w in Solvesso 100) | Dodecyl isocyanate | 50 | Yes | Not tested | 6.0 |
| Jeffamine M-1000 | Fluazifop-p-butyl (50% w/w) in Solvesso 200 | P = Tolyl isocyanate | 50 | Yes | Not tested | 3.0 |
| Poly EPS-520 Na | Lambda-cyhalothrin (75% solution in Solvesso 100) | p-Tolyl isocyanate | 50 | Yes | Not tested | 3.0 |

-continued

| Amine | Oil phase | Isocyanate | % oil phase | Initial emulsion formed? | Longer term stability? | D(v, 0.5)/ microns |
|---|---|---|---|---|---|---|
| Poly EPS-520 Na | Fluazifop-p-butyl (50% w/w) in Solvesso 200 | p-Tolyl isocyanate | 50 | Yes | Not tested | 2.0 |
| Poly EPS-520 Na | Picoxystrobin (25% w/w in Solvesso 200 | p-Tolyl isocyanate | 50 | Yes | Not tested | 7.0 |
| Poly EPS-520 Na | Picoxystrobin (25% w/w in Solvesso 200 | p-Tolyl isocyanate | 20 | Yes | Not tested | 6.0 |
| Poly EPS-520 Na | Picoxystrobin (25% w/w in Solvesso 200 | Dodecyl isocyanate | 20 | Yes | Not tested | 6.0 |
| Poly EPS-520 Na Comparative Example (f) | Solvesso 200 | none | 50 | Did not emulsify | | |

These examples illustrate the ability to form stable emulsions starting from no surfactant but reacting the reactive isocyanate together with a non-surfactant amine at the oil-water interface, thus forming a bound surfactant at the interface and having no free surfactant available in the continuous aqueous phase. The examples illustrate the preparation and use on non-ionic and anionic surfactant species. Other surfactant types are within the ability of those skilled in the art. The comparative examples show that M-2070 has slight emulsification characteristics but (as with DNIP) but also that as a free base (as also with D-400), these can react with any residual free oleic acid in methyl oleate to produce a soap which acts as the emulsifier in those comparative examples ((c) and (d)). However, using D-400 with a poorly water soluble oil with no free acid (comparative example (f)) shows no emulsification. Thus only the combination of reactive components (eg isocyanates plus amines with an oil phase result in useful products.

Although this invention has been described with respect to specific embodiments, the details hereof are not to be construed as limitations, for it will be apparent that various, equivalents, changes and modifications may be resorted to without parting from the spirit and scope of the invention, and it is understood that such equivalent embodiments are intended to be included within the scope of the invention.

What is claimed is:

1. An emulsion comprising a dispersed phase droplet having a surfactant layer at the interface with the continuous phase wherein said surfactant layer is formed by the reaction of the wall-forming moieties of a microcapsule wall-forming material with an interface modifying compound selected from compounds having a formula (I), (II), (III) (IV) or (V)

X-z (I)

X-z-X (II)

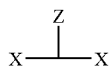 (III)

X—X-z (IV)

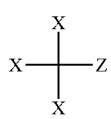 (V)

wherein Z is a moiety that contributes to modifying the surface properties of said emulsion and each X is, independently, a functional moiety capable of reacting with the wall-forming moieties of a wall-forming material and the moieties designated by lines linking the X and Z functional groups have a molecular weight of between 50 and 4000, and may be optionally substituted aryl, hydrocarbyl, or heterocyclic units, or combinations thereof, optionally containing internally linked amino, ether, thioether, acetal, ester, thioester, amide, sulphonamide, urethane, urea, carbonate, siloxane, or phosphonamide groups or combinations thereof and wherein substantially all of the wall-forming moieties of the wall-forming material are reacted with one or more groups —X of the interface modifying compound such that little or no wall-forming functionality remains after reaction, provided that the wall forming material is not a urea formaldehyde.

2. An emulsion according to claim 1 wherein —X in structures (I) to (III) and (V) is hydroxyl, thiol, a group —NHA wherein A is hydrogen or $C_1$ to $C_4$ alkyl or a group —CO—OR where R is hydrogen or a hydrocarbyl moiety having 1-30 carbon atoms optionally linked or substituted by one or more halo, amino, ether or thioether groups or combinations of these or wherein in structure (IV) —X— is —NH—.

3. An emulsion according to claim 1 or 2 wherein -Z comprises sulphonate, carboxylate, phosphonate, phosphate, quaternary ammonium, betaine, oxyethylene or an oxyethylene-containing polymer.

4. An emulsion according to claim 3 wherein
when -Z is sulphonate, carboxylate, phosphonate or phosphate it is present as a salt providing the $-Z^-$ anion or
wherein when -Z is quaternary ammonium it has the structure $$[-NR_1R_2R_3]^+A'^-$$

wherein $R_1$, $R_2$ and $R_3$ are independently hydrogen or $C_1$ to $C_4$ alkyl and $A'^-$ is a suitable inorganic or organic anion such as halide or acetate provided that not more than one of $R_1$, $R_2$ and $R_3$ is hydrogen
or wherein
when -Z is oxyetheylene or an oxyethylene-containing polymer, it is an oxyethylene polymer or a random or block oxyethylene/oxypropylene copolymer containing an oxyethylene to oxypropylene ratio of grater than 1.

5. An emulsion according to claim 1 wherein the interface modifying compound of structure (I) has the formula $$X—Y_1-Z \quad \text{(IA)}$$

wherein $Y_1$ represents the moiety linking X and Z and is a straight or branched chain alkyl linking group containing from 1 to 20 carbon atoms; or is phenyl, naphthyl, cyclopentyl or cyclohexyl;
or wherein when Z is an oxyethylene containing polymer and $Y_1$ represents a direct link between X and Z the interface modifying compound of structure (I) has a formula (IB)

$$R_4—O(PO)_r(EO)_s—X \quad \text{(IB)}$$

wherein $R_4$ is an end-capping group which is $C_1$ to $C_4$ alkyl, r, and s are independently from 0 to 3000, provided that s is not 0 and the total of r+s is from about 7 to about 3000 and EO and PO represent oxyethylene and oxypropylene respectively which may be arranged in random or block formation;
or wherein when Z is an oxyethylene/oxypropylene block copolymer and $Y_1$ represents a direct link between X and Z the interface modifying compound of structure (I) has formula (IC)

$$R_{4'}—O(PO)_{r'}(EO)_{s'}(PO)_t—X \quad \text{(IC)}$$

wherein $R_{4'}$ is an end-capping group which is $C_1$ to $C_4$ alkyl, r', s' and t are independently from 0 to 2000, provided that s is not 0 and the total of r'+s'+t is from about 7 to about 3000 and EO and PO represent oxyethylene and oxypropylene respectively;
or wherein when $Y_1$ is a ring structure group, the interface modifying compound of structure (I) has a formula (ID)

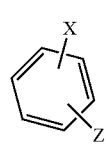

(ID)

wherein X and Z are as defined previously or if X and Z are adjacent substituents capable of reacting together they may form a cyclic anhydride capable of ring-opening under the reaction conditions.

6. An emulsion according to claim 1 wherein the interface modifying compound of structure (II) wherein -Z- is an oxyethylene containing polymer and there is a direct bond between -Z- and each —X has the formula (IIA)

$$X—(EO)_a(PO)_b—X' \quad \text{(IIA)}$$

wherein a and b are independently from 0 to 3000, provided that a is not 0 and the total of a+b is from about 7 to about 3000 and EO and PO represent oxyethylene and oxypropylene respectively which may be arranged in random or block formation; or
wherein the interface modifying compound of structure (II) wherein -Z- is an ethylene oxide, propylene oxide block copolymer and there is a direct bond between -Z- and each X has the formula (IIB)

$$X—(PO)_{a'}(EO)_{b'}(PO)_c—X' \quad \text{(IIB)}$$

wherein a', b' and c are independently from 0 to 2000, provided that b' is not 0 and the total of a'+b'+c is from about 7 to about 3000 and EO and PO represent oxyethylene and oxypropylene respectively; or
wherein -Z- in structure (II) is quaternary ammonium and structure (II) has the formula (IIC)

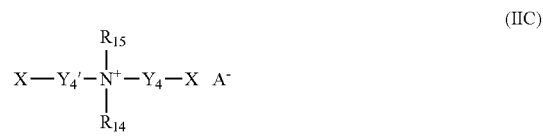

(IIC)

wherein $R_{14}$ and $R_{15}$, which may be the same or different, are hydrogen $C_1$ to $C_{20}$ straight or branched chain alkyl; aryl; or $C_1$ to $C_4$ aralkyl, wherein each aryl group may be optionally substituted by $C_1$ to $C_4$ alkyl, nitro or halo and $Y_4$ and $Y_{4'}$ which may be the same or different are —$R_8$— or —$R_7$-$(L_1)_n$- wherein $R_7$, and $R_8$ are independently $C_1$ to $C_{10}$ straight or branched chain alkyl linking groups optionally substituted by halogen or $C_1$ to $C_4$ alkoxy and $(L_1)_n$ is a polyoxyalkyene group; n is from 2 to 20 and A— is a suitable anion.

7. An emulsion according to claim 1 wherein the interface modifying compound of structure (III) has a formula (IIIA)

$$X—Y_2—C(Z)(R_6)—Y_{2'}X' \quad \text{(IIIA)}$$

wherein $R_6$ is hydrogen or more preferably a $C_1$ to $C_4$ alkyl group optionally substituted by ether, for example $C_1$ to $C_4$ alkoxy or halogen and $Y_2$ and $Y_{2'}$, which may be same or different are independently —$R_7$-$(L_1)$n- or

—$R_8$— wherein $R_7$, and $R_8$ are independently $C_1$ to $C_{10}$ straight or branched chain alkyl linking groups optionally substituted by halogen or $C_1$ to $C_4$ alkoxy and $(L_1)_n$ is polyoxyethylene, polyoxypropylene or polyoxybutylene; n is from 2 to 20, preferably from 4 to 10; or wherein the interface modifying compound of structure (III) wherein the moiety linking X and Z is a ring structure group has a formula (IIIB) or (IIIC)

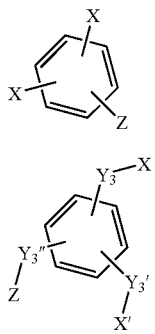

(IIIB)

(IIIC)

wherein $Y_3$, $Y_{3'}$ and $Y_{3''}$ individually represent a direct link between X' or Z (as the case may be) and the ring structure or may be a group

-($L_2$)- $R_9$ where $L_2$ is an ester linking group —C(O)—O—, $R_9$ is oxyethylene, oxypropylene or oxybutylene or polyoxyethylene, polyoxypropylene or polyoxybutylene having a degree of polymerisation from 2 to 20; or wherein the interface modifying compound of structure (III) has the formula (IIID)

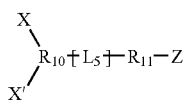

(IIID)

wherein $R_{10}$ is a $C_1$ to $C_8$ straight or branched chain alkyl group and the two groups X and X', which may be the same or different, may be attached to the same carbon atom in the alkyl chain or to different carbon atoms in the alkyl chain, and -$L_5$- is a linking group which is -($L_1$)$_n$- or

—$R_8$— wherein $R_8$, and ($L_1$)$_n$ are as defined above in relation to formula (IIIA) and $R_{11}$ is $C_1$ to $C_4$ alkyl.

8. An emulsion according to claim 1 wherein the interface modifying compound of structure (IV) has a formula (IVA)

X—Y—NH—Y'—Z  (IVA)

wherein Y and Y' are independently a straight or branched chain $C_1$ to $C_{10}$ alkyl group, a polyoxyethylene, poly-oxypropylene or polyoxybutylene polymer chain of formula -($L_1$)$_n$ - as defined above or a group -($L_2$)-$R_9$— as defined above.

9. An emulsion according to claim 1 wherein the interface modifying compound is a sulfonate polyester polyol prepared by reacting sodium sulphoisophthalic acid, adipic acid, cyclohexane dimethanol, methoxy-polyethylene glycol (MW750) and trimethylol propane to give a product having a hydroxyl number in the range of from 150 to 170.

10. An emulsion according to claim 1 wherein the wall forming material is an isocyanate wall forming material.

11. An emulsion according to claim 10 wherein the isocyanate wall forming material is selected from tolylene diisocyanate and isomers thereof, phenylene diisocyanate and isomers thereof, biphenylene diisocyanates and isomers thereof, polymethylenepolyphenyleneisocyanates (PMPPI), aliphatic hexamethylene diisocyanate and timers thereof (HMDI), isophoronediisocyanate (IPDI), p-tolyl isocyanate, dodecyl isocyanate and hexadecyl isocyanate and mixtures of such isocyanates.

12. A process for forming an emulsion which comprises reacting an interface modifying compound having a formula (I), (II), (III), (IV) or (V) as defined in claim 1 with a microcapsule wall-forming material wherein substantially all of the wall-forming moieties of the wall-forming material are reacted with one or more groups —X of the interface modifying compound such that little or no wall-forming functionality remains after reaction and subsequently or simultaneously producing an emulsion using the surfactant reaction product.

13. A process according to claim 12 wherein the reaction of the interface modifying compound and the wall-forming material takes place in an organic phase as a pre-reaction, the resultant surfactant being either isolated or used in solution in the organic phase, and thereafter emulsifying an oil phase containing the surfactant product into water.

14. A process according to claim 12 wherein the interface modifying compound and the wall-forming material are reacted in an organic phase after emulsification has taken place.

15. A process according to claim 12 where the wall-forming material is dissolved in an oil phase which is dispersed in water, optionally in the presence of additional surfactants and optionally in the presence of any material to be contained in the dispersed oil phase, whilst the interface modifying compound is added to the aqueous continuous phase and thereafter the interface modifying compound and the wall-forming material react at the interface of the continuous phase and the dispersed phase droplets to form the surfactant.

* * * * *